US00PP23206P2

(12) United States Plant Patent
Hurkman

(10) Patent No.: US PP23,206 P2
(45) Date of Patent: Nov. 20, 2012

(54) ***PETUNIA* PLANT NAMED 'BALSPUNLU'**

(50) Latin Name: *Petunia×hybrida*
Varietal Denomination: Balspunlu

(75) Inventor: Margaret M. Hurkman, Santa Maria, CA (US)

(73) Assignee: Ball Horticultural Company, West Chicago, IL (US)

( * ) Notice: Subject to any disclaimer, the term of this patent is extended or adjusted under 35 U.S.C. 154(b) by 35 days.

(21) Appl. No.: 13/134,209

(22) Filed: Jun. 1, 2011

(51) Int. Cl.
*A01H 5/00* (2006.01)

(52) U.S. Cl. ..... Plt./356.16; Plt./356.1

(58) Field of Classification Search ..... Plt./356.1, Plt./356.16
See application file for complete search history.

*Primary Examiner* — Susan McCormick Ewoldt
(74) *Attorney, Agent, or Firm* — Audrey Charles

(57) ABSTRACT

A new and distinct cultivar of *Petunia* plant named 'Balspunlu', characterized by its dark violet-blue colored flowers, dark green-colored foliage, low vigor, and compact, upright-mounded growth habit, is disclosed.

1 Drawing Sheet

Latin name of genus and species of plant claimed: *Petunia×hybrida.*

Variety denomination: 'Balspunlu'.

BACKGROUND OF THE INVENTION

The present invention relates to a new and distinct cultivar of *Petunia* plant botanically known as *Petunia×hybrida* and hereinafter referred to by the cultivar name 'Balspunlu'.

The new cultivar originated in a controlled breeding program in Arroyo Grande, Calif. during June 2006. The objective of the breeding program was the development of *Petunia* cultivars with single type flowers, unique flower coloration, and compact, upright-mounded growth habit.

The new *Petunia* cultivar is the result of cross-pollination. The female (seed) parent of the new cultivar is the proprietary *Petunia×hybrida* breeding selection designated 4118-2, not patented, characterized by its dark purple-colored flowers, dark green-colored foliage, and vigorous, trailing growth habit. The male (pollen) parent of the new cultivar is the proprietary *Petunia×hybrida* breeding selection designated 3130-2-2, not patented, characterized by its dark blue-colored flowers, dark green-colored foliage, and moderately vigorous, semi-upright growth habit. The new cultivar was discovered and selected as a single flowering plant within the progeny of the above stated cross-pollination during May 2007 in a controlled environment in Arroyo Grande, Calif.

Asexual reproduction of the new cultivar by terminal stem cuttings since May 2007 at Arroyo Grande, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balspunlu' as a new and distinct cultivar of *Petunia* plant:

1. Dark violet-blue colored flowers;
2. Dark green-colored foliage;
3. Low vigor; and
4. Compact, upright-mounded growth habit.

Plants of the new cultivar differ from plants of the female parent primarily in flower color, growth vigor, and growth habit and from plants of the male parent primarily in flower size, growth vigor, and habit. Plants of the new cultivar have a bluer flower color, reduced growth vigor, and a more compact-mounded growth habit than plants of the female parent. Plants of the new cultivar have larger-sized flowers, reduced growth vigor, and a more compact-mounded growth habit than plants of the male parent.

Of the many commercially available *Petunia* cultivars, the most similar in comparison to the new cultivar is POTUNIA Deep Purple 'Duepotdepur', U.S. Plant Pat. No. 19,294. However, in side by side comparisons, plants of the new cultivar differ from plants of 'Duepotdepur' in at least the following characteristics:

1. Plants of the new cultivar have a darker and more violet flower color than plants of 'Duepotdepur'; and
2. Plants of the new cultivar have smaller leaves, as measured by length and width, than plants of 'Duepotdepur'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balspunlu'. The plants were grown in 4-inch pots for 6 weeks in a greenhouse at West Chicago, Ill. Plants were given one pinch one week after transplant.

DETAILED BOTANICAL DESCRIPTION

Figure 1:
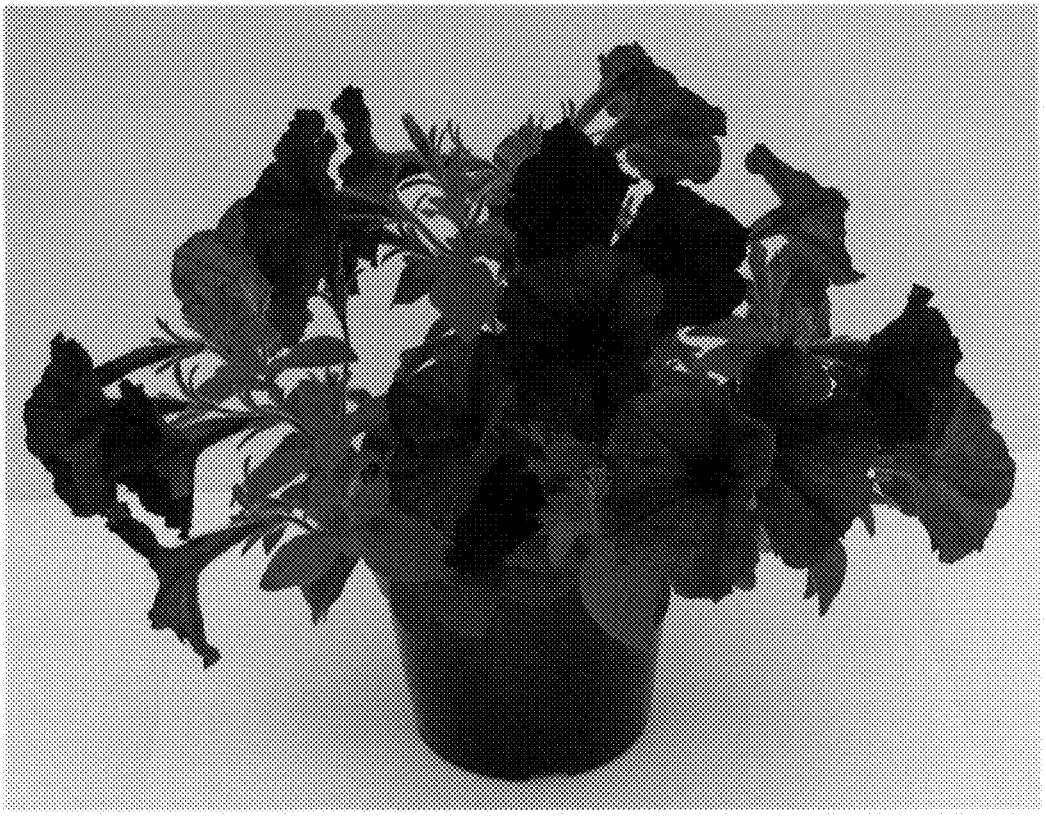
FIG. 1 illustrates a side view of the overall growth and flowering habit of 'Balspunlu'.
Figure 2:
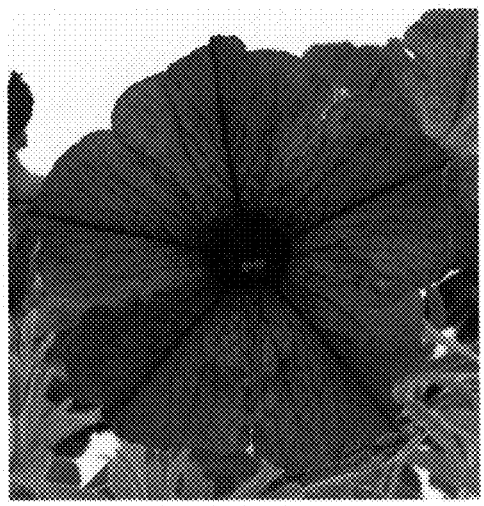
FIG. 2 illustrates a close-up view of an individual flower of 'Balspunlu'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in March 2011 under natural light conditions in West Chicago, Ill.

The following descriptions and measurements describe plants produced from cuttings from stock plants and grown in a glass-covered greenhouse under conditions comparable to those used in commercial practice. The plants were grown in West Chicago, Ill. in 4-inch pots for 6 weeks utilizing a soilless growth medium. Plants were given one pinch one week after transplant. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day. Measurements and numerical values represent averages of typical plants.

Botanical classification: *Petunia×hybrida* cultivar 'Balspunlu'.

Parentage:

*Female parent*.—Proprietary *Petunia×hybrida* breeding selection designated 4118-2, not patented.

*Male parent*.—Proprietary *Petunia×hybrida* breeding selection designated 3130-2-2, not patented.

Propagation:

*Type cutting*.—Terminal stem.

*Time to initiate roots*.—Approximately 6 to 9 days.

*Time to produce a rooted cutting*.—Approximately 21 to 28 days.

*Root description*.—Fibrous.

*Rooting habit*.—Freely branching.

Plant description:

*Commercial crop time*.—Approximately 6 to 8 weeks from a rooted cutting to finish in a 10 cm pot.

*Growth habit and general appearance*.—Low vigor, compact, upright-mounded.

*Size*.—Height from soil level to top of plant plane: Approximately 14.4 cm. Width: Approximately 26.4 cm.

*Branching habit*.—Freely branching, pinching improves basal branching. Quantity of main branches per plant: Approximately 6.

*Branch*.—Strength: Moderate. Length: Approximately 14.6 cm. Diameter: Approximately 3.0 mm. Length of central internode: Approximately 1.6 cm. Texture: Densely glandular pubescent with a mixture of long and short length hairs: Gland color: Colorless. Color of young and mature stems: 144A.

Foliage description:

*General description*.—Quantity of leaves per main branch: Approximately 14. Fragrance: Slight. Form: Simple. Arrangement on flowering stem: Opposite.

*Leaves*.—Aspect: Perpendicular to acute angle to stem. Shape: Ovate to elliptic. Margin: Entire. Apex: Acute. Base: Attenuate. Venation pattern: Pinnate. Length of mature leaf: Approximately 4.6 cm. Width of mature leaf: Approximately 2.7 cm. Texture of upper and lower surfaces: Moderately glandular pubescent. Gland color: Colorless. Color of upper surface of young and mature foliage: 137A with venation of 144B. Color of lower surface of young and mature foliage: 138B with venation of 144B.

*Petiole*.—Length: Approximately 6.0 mm. Width: Approximately 2.0 mm. Texture: Densely glandular pubescent with a mixture of long and short length hairs. Gland color: Colorless. Color: 144B.

Flowering description:

*Flowering habit*.—'Balspunlu' is freely flowering under outdoor growing conditions with substantially continuous blooming from spring through autumn and year-round in greenhouse environment.

*Lastingness of individual flower on the plant*.—Approximately 10 to 12 days.

Flower description:

*General description*.—Type: Simple, salverform. Quantity per plant: Approximately 18. Fragrance: Slight.

*Bud*.—Rate of opening: Generally takes 2 to 3 days for bud to progress from first color to fully open flower. Quantity per plant: Approximately 5.

*Bud just before opening*.—Shape: Oblong. Length: Approximately 3.8 cm. Diameter at apex: Approximately 9.0 mm. Diameter at base: Approximately 3.0 mm. Texture: Densely glandular pubescent. Gland color: Colorless. Color of petals: N92D. Color of tube: N92D with venation of N92A.

*Corolla*.—Diameter: Approximately 6.3 cm.

*Petals*.—Quantity: 5, fused to form a tube. Shape: Obovate. Appearance: Velvety. Margin: Entire, slightly wavy. Apex: Emarginate. Length from tube: Approximately 2.8 cm. Length of free portion: Approximately 1.4 cm. Width: Approximately 3.2 cm. Texture of upper surface: Glabrous. Texture of lower surface: Sparsely glandular pubescent. Gland color: Colorless. Color of upper surface when first open: Darker than N89A with venation of N186A. Color of lower surface when first and fully open: Closest to 90A with venation of N92A. Color of upper surface when fully open: Closest to N89A with midveins of N186A.

*Corolla tube*.—Length: Approximately 3.2 cm. Diameter at distal end: Approximately 1.0 cm. Diameter at proximal end: Approximately 3.0 mm. Texture of inner surface: Glabrous. Texture of outer surface: Densely glandular pubescent. Gland color: Colorless. Color of inner surface: Darker than N92A with venation of Darker than N92A. Color of outer surface: Darker than N92D with venation of N92A.

*Sepals*.—Quantity per flower: 5, fused at base. Shape: Linear. Apex: Acute. Length: Approximately 1.9 cm. Width: Approximately 3.0 mm. Texture of upper and lower surfaces: Densely glandular pubescent. Gland color: Colorless. Color of upper surface: 137A. Color of lower surface: 137C transitioning to 144B at base.

*Peduncle*.—Strength: Strong. Aspect: Acute angle to stem. Length: Approximately 2.7 cm. Diameter: Approximately 2.0 mm. Texture: Densely glandular pubescent with a mixture of long and short length hairs. Gland color: Colorless. Color: 144A, occasionally with an overlay of 187B nearest sepals.

*Reproductive organs*.—Androecium: Stamen quantity: 5, basifixed. Stamen length: Approximately 2.5 cm. Filament length of fixed portion: Approximately 9.0 mm. Filament color: 155D with an overlay of 79B. Anther shape: Bilobed. Anther length: Approximately 1.0 mm. Anther color: N92D. Pollen amount: Abundant. Pollen color: 93C. Gynoecium: Pistil quantity: 1 per flower. Pistil length: Approximately 2.6 cm. Stigma shape: Funnel. Stigma length: Approximately 2.0 mm. Stigma color: 146A ages to N92A; 79A at base. Style length: Approximately 2.1 cm. Style color: 145D with an overlay of 79B. ovary length: Approximately 3.0 mm. Ovary color: 144C.

Seed and fruit production: Neither seed nor fruit production has been observed.

Disease and pest resistance: Resistance to pathogens and pests common to *Petunia* has not been observed.

What is claimed is:

1. A new and distinct cultivar of *Petunia* plant named 'Balspunlu', substantially as herein shown and described.

* * * * *